Figure 1:
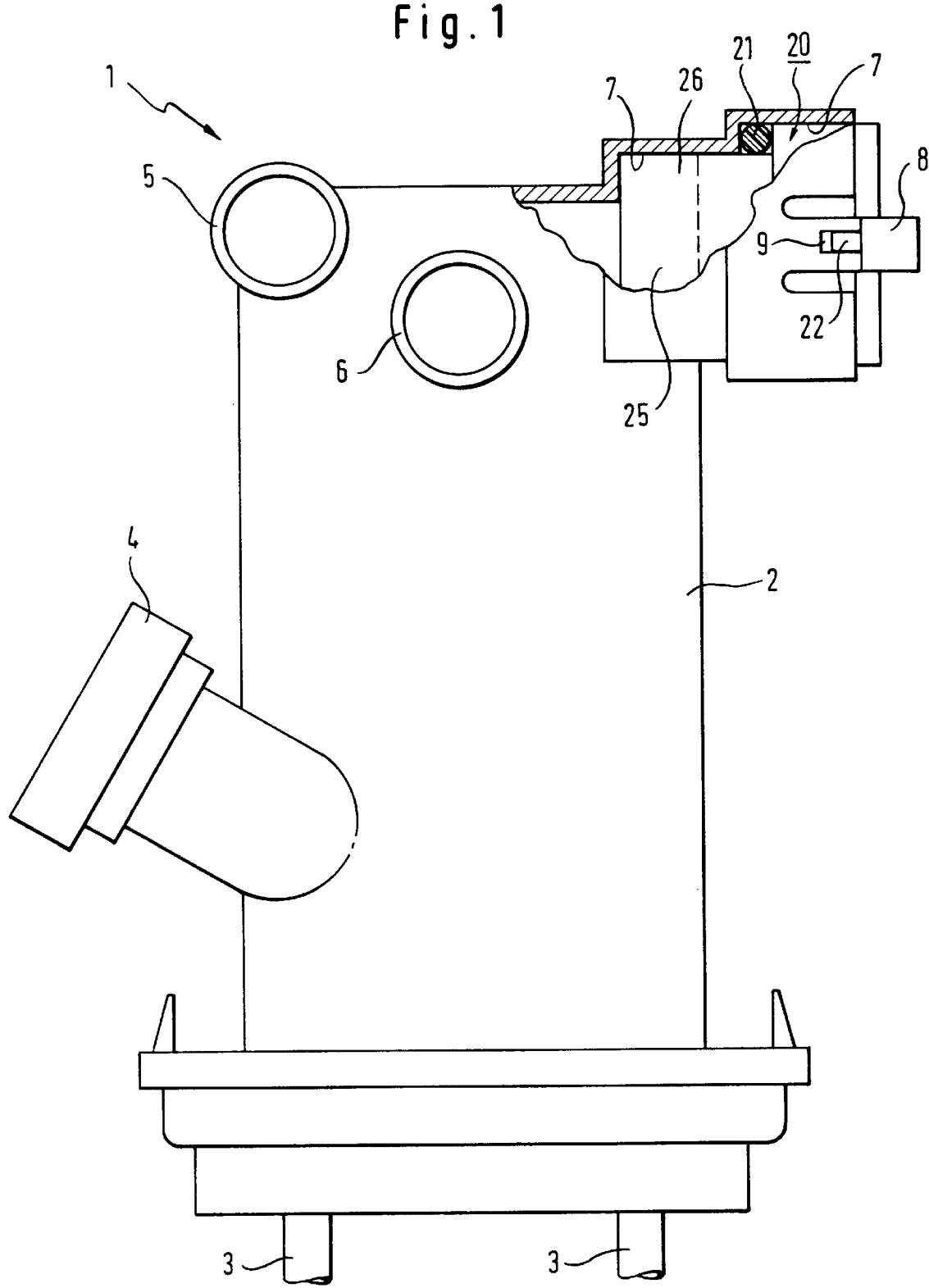

United States Patent [19]
Wilhelmstätter et al.

[11] Patent Number: 5,818,063
[45] Date of Patent: Oct. 6, 1998

[54] OPTICAL SENSOR FOR CONTAMINATION IN A CIRCULATING CLEANING FLUID

[75] Inventors: Johann Wilhelmstätter, Giengen/Hürben; Helmut Jerg, Giengen; Bernd Schessl, Dillingen; Gerhard Fetzer, Gundelfingen; Michael Hartmann, Höchstädt; Markus Höpfl, Lauingen/Donau; Karl-Heinz Rehm, Dischingen; Rudolf Schmidt, Giengen, all of Germany

[73] Assignee: BSH Bosch und Siemens Hausgeraete GmbH, Munich, Germany

[21] Appl. No.: 821,034

[22] Filed: Mar. 20, 1997

[51] Int. Cl.⁶ .................................................. G01N 15/06
[52] U.S. Cl. .......................................... 250/573; 356/442
[58] Field of Search ...................................... 250/573, 574; 356/436, 442; 73/61.41, 61.48, 61.69

[56] References Cited

U.S. PATENT DOCUMENTS 5,619,333  4/1997  Staff et al. ............................... 356/436

Primary Examiner—Que Le
Attorney, Agent, or Firm—Herbert L. Lerner; Laurence A. Greenberg

[57] ABSTRACT

In order to provide in a simple way a household appliance, operated with water with a sensor (10) for contaminations of a circulated cleaning fluid, said sensor being composed of an element (11) transmitting optical signals and of an element (12) receiving optical signals, in which appliance erroneous measurements of the sensor (10) for contaminations of a circulated cleaning fluid are avoided, according to the invention the sensor (10) is arranged in a flow heater (1).

15 Claims, 2 Drawing Sheets

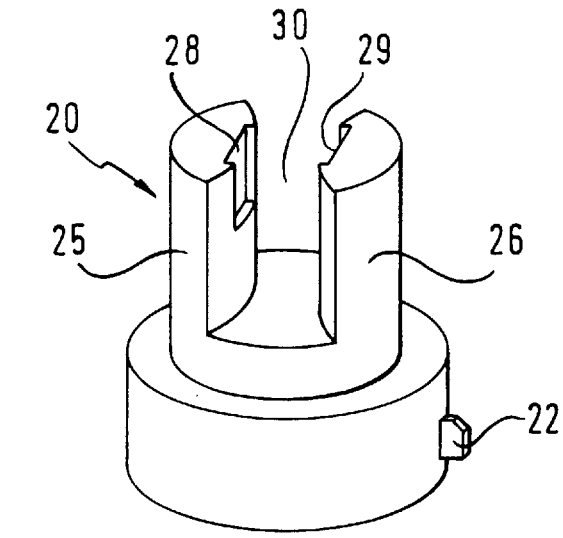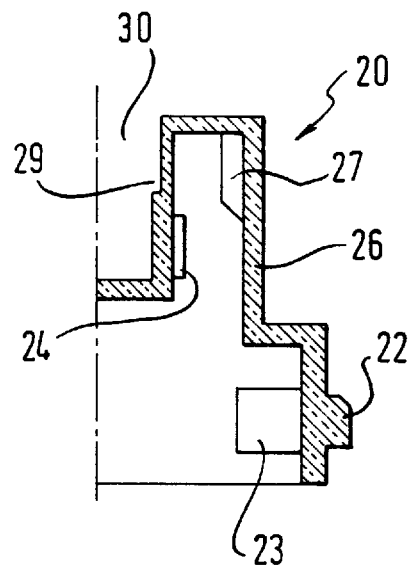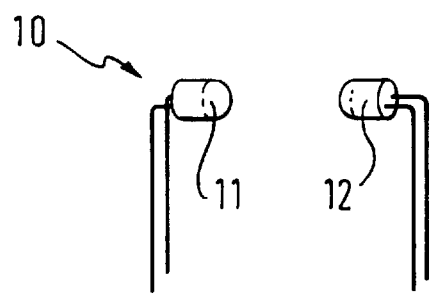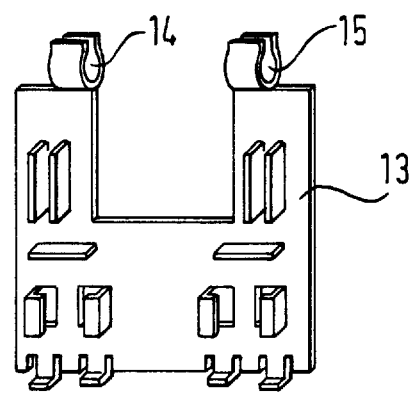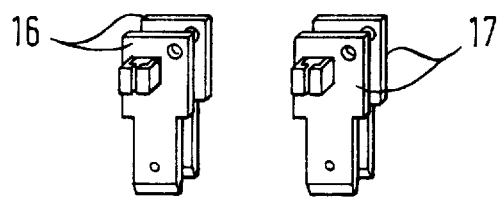

OPTICAL SENSOR FOR CONTAMINATION IN A CIRCULATING CLEANING FLUID

The invention relates to a household appliance operated with water, with a sensor for contaminations of a circulated cleaning fluid, said sensor being composed of an element transmitting optical signals and of an element receiving optical signals.

A household appliance operated with water employs an abovementioned sensor for measuring the contamination of the cleaning fluid, in order to influence the cycle of the washing or rinsing program on the basis of the measured degree of contamination.

U.S. Pat. No. 3,888,269 discloses, for example, a household appliance operated with water, namely a dishwasher, with a sensor for contaminations of a circulated cleaning fluid, said sensor being composed of an element transmitting optical signals and of an element receiving optical signals, in which dishwasher the sensor is arranged under a transparent portion of a horizontal step of a treatment vessel, the transparent portion being surrounded by an upstanding edge.

Despite the movement of the circulated cleaning fluid, deposits of dirt particles may accumulate on a horizontal step of the treatment vessel. In particular, in the prior art described above, the upstanding edge of the transparent portion leads to accumulations of dirt particles precisely in the region in which the optical sensor carries out measurements. The cleaning fluid remaining on the horizontal step evaporates, this being assisted, in a household appliance operated with water, by the high temperature which prevails during the cycle of the washing or rinsing program. Depending on the degree of hardness of the cleaning fluid used, a lime deposit is formed during the evaporation of the remaining cleaning fluid. In particular, in the prior art described above, the upstanding edge of the transparent portion leads to accumulations of cleaning fluid precisely in the region in which the optical sensor carries out measurements, the fluid leaving behind lime deposits in the measuring region of the sensor during evaporation. Deposits of lime and accumulations of dirt particles on the transparent portion lead to falsifications of the measurement result of the sensor. On the horizontal step of the treatment vessel according to the prior art described above there is no exchange of cleaning fluid in conformity with its circulation, so that the actually existing degree of contamination of the cleaning fluid is not established and falsifications of the measurement result of the sensor also occur as a result. In particular, in the prior art described above, the upstanding edge of the transparent portion leads to accumulations of cleaning fluid precisely in the region in which the optical sensor carries out measurements, these accumulations, if they remain there for a relatively long time, not having the actually existing degree of contamination of the cleaning fluid, thus leading to falsifications of the measurement result of the sensor.

The object on which the invention is based is therefore to provide in a simple way a household appliance operated with water of the initially mentioned type, in which erroneous measurements of a sensor for contaminations of a circulated cleaning fluid are avoided.

This object is achieved, according to the invention, in that the sensor is arranged in a flow heater.

A flow heater is a means arranged in the flow path of a circulated cleaning fluid of a household appliance operated with water and intended for heating the circulated cleaning fluid. During parts of the cleaning program which involve a circulation of cleaning fluid, therefore, the cleaning fluid flows constantly through the flow heater and has the actually existing degree of contamination of the cleaning fluid, which can be recorded by the sensor. The constant throughflow completely rules out an accumulation of dirt. The flow heater normally remains completely filled with cleaning fluid, even during breaks in circulation, and also during standstill, of the household appliance operated with water, so that an evaporation of a residual quantity of a cleaning fluid, and consequently a deposit of lime occurring during evaporation, do not take place. According to the invention, the sensor for contaminations of a circulated cleaning fluid is arranged at a location which has a specific exchange of cleaning fluid and at which there is no risk that dirt or lime will be deposited. The arrangement according to the invention of the sensor in a flow heater results, in a simple way, in a household appliance operated with water of the initially mentioned type, in which erroneous measurements of a sensor for contaminations of a circulated cleaning fluid are effectively avoided.

According to a preferred feature of the invention, the flow heater has a separate receiving connection piece for the sensor, thereby making it possible for the flow heater to have a simple design.

According to a further feature of the invention, the sensor is arranged in a receptacle which is introduced into the receiving connection piece of the flow heater. This measure achieves a further simplification in the design of the flow heater and also in the assembly of the flow heater, since preassembly and also a simple insertion of the sensor become possible.

Advantageously, the receptacle has essentially a round cross section, with the result that the shape of the receiving connection piece and consequently the manufacture of the flow heater are further simplified.

In a particularly advantageous way, the receptacle is produced from at least milky-transparent material, as a result of which a further possible source of error, namely the effect of the material through which the optical signals must pass, is, as far as possible, ruled out.

The receptacle is expediently completely closed at its end projecting into the flow heater, thereby avoiding direct contact of the sensor with the cleaning fluid and consequently ensuring additional reliability in the functioning of the sensor.

According to a preferred embodiment of the invention, the sensor is fastened on a conductor plate, the elements of the sensor being arranged opposite and facing one another. This embodiment achieves a simplified production and assembly of the sensor.

The receptacle expediently has at least one guide, into which the conductor plate can be pushed, this making assembly even easier.

The guide is preferably composed of mounting ribs arranged in pairs at a spacing corresponding to the thickness of the conductor plate, thus allowing the receptacle to be produced in a simple way.

According to a further feature of the invention, the receptacle has two legs which are arranged at a mutual spacing and in which an element of the sensor is arranged in each case. This measure defines a better measurement section than the prior art initially described, since the optical signals from the transmitter to the receiver pass in one direction essentially only through the cleaning fluid to be assessed flowing through between the two legs.

In a particularly advantageous way, the legs have essentially a cross-sectional shape of segments of a circle which rest with their chords against one another, with the result that a sharp outer edge is formed and all the outer faces of the legs are rounded and with the result that the settling of deposits is ruled out to the greatest extent.

In order, as far as possible, to rule out the one further possible source of error, namely the effect of the material through which the optical signals must pass, in each case a portion of those walls of the legs which form the limitation of the interspace advantageously has a smaller wall thickness than the wall thickness of the remaining parts of the receptacle.

Preferably, the receptacle is sealed off in the receiving connection piece by means of an O-ring, thereby achieving a further simplification in assembly.

The receptacle is advantageously fastened to the flow heater by means of a snap connection, thus making assembly even easier.

The snap connection is expediently composed of at least one spring tab which projects from the receiving connection piece and which has an orifice, into which a catching boss of the receptacle drops, thus affording a further simplification in production and assembly.

The invention is explained below with reference to the exemplary embodiment illustrated in the drawing, in which FIG. 1 shows a diagrammatic illustration of a flow heater of a household appliance operated with water according to the invention, FIG. 2 shows an exploded illustration of the arrangement of a sensor in a receptacle, and FIG. 3 shows a half section through the receptacle.

A household appliance operated with water, not described in any more detail, has a flow heater 1 for heating a circulated cleaning fluid, said flow heater having heating elements 3 arranged in a closed housing 2, an inlet connection piece 4 and at least one outlet connection piece, in the exemplary embodiment shown two outlet connection pieces 5, 6.

According to the invention, a sensor 10 for contaminations of a circulated cleaning fluid is arranged in the flow heater 1, said sensor being composed of an element 11 transmitting optical signals and of an element 12 receiving optical signals. For this purpose, the flow heater 1 has a separate receiving connection piece 7 for the sensor 10, in which the sensor 10, which is inserted into a receptacle 20, milky-transparent in the exemplary embodiment shown, is introduced and is sealed off by means of an 0-ring 21. The receptacle 20 is fastened to the flow heater 1 by means of a snap connection which is composed of two spring tabs 8 which project from the receiving connection piece 7 and which have in each case an orifice 9, into which a catching boss 22 of the receptacle 20 drops in each case.

As can be seen in FIG. 2, the sensor 10 is fastened on a conductor plate 13, the elements 11, 12 of the sensor 10 being arranged opposite and facing one another in clamping receptacles 14, 15, the feed lines of which are fastened in each case by means of holding devices and guides, not described in any more detail, and, at that end of the conductor plate 13 which is located opposite the clamping receptacles 14, 15, in each case by means of two-part junction terminals 16, 17.

As can best be seen in FIG. 3, the receptacle 20 has guides, into which the conductor plate 13 can be pushed and which are composed of mounting ribs 23, 24 arranged in pairs at a spacing corresponding to the thickness of the conductor plate 13.

The receptacle 20 has two legs 25, 26 arranged at a mutual spacing a, thereby forming an interspace 30 which constitutes the measurement section of the sensor 10. An element 11, 12 of the sensor 10 is therefore arranged in each case in the legs 25, 26, as can best be seen in FIG. 2. In the exemplary embodiment shown, the legs 25, 26 have, in cross section, essentially a shape of segments of a circle which rest with their chords against one another. Arranged at the closed end of each leg 25, 26 in each case is a fixing rib 27 (FIG. 3) which presses the corresponding element 11, 12 of the sensor 10 into bearing contact against the opposite inner wall of the corresponding leg 25, 26, in each case a portion 28, 29 of that wall of the legs 25, 26 which forms the limitation of the interspace 30, the corresponding element 11, 12 of the sensor 10 resting against said wall portion, having a smaller wall thickness than the wall thickness of the remaining parts of the receptacle 20, as can best be seen in FIG. 3.

The flow heater 1 according to the exemplary embodiment described is arranged in the flow path of a circulated cleaning fluid of the household appliance operated with water according to the invention, for the purpose of heating the circulated cleaning fluid. During a part of the cleaning program which involves a circulation of cleaning fluid, therefore, the cleaning fluid flows constantly through the flow heater 1. This cleaning fluid flowing through the flow heater 1 has the actually existing degree of contamination of the cleaning fluid, so that the sensor can record this. The constant throughflow completely rules out an accumulation of dirt. The flow heater 1 normally remains completely filled with cleaning fluid during breaks in circulation, and even during standstill, of the household appliance operated with water, so that an evaporation of a residual quantity of a cleaning fluid, and consequently a deposit of lime occurring during evaporation, do not take place. According to the invention, the sensor 10 for contaminations of the circulated cleaning fluid is arranged at a location which has a specific exchange of cleaning fluid and at which there is no risk that dirt or lime will be deposited. The arrangement according to the invention of the sensor 10 in the flow heater 1 results in a simple way in a household appliance operated with water of the initially mentioned type, in which faulty measurements of the sensor are effectively avoided.

We claim:

1. In a water-conducting household appliance of the type having a flow heater and wherein a degree of contamination in a circulating cleaning fluid is measured during operation of the appliance, the improvement which comprises:
   a sensor for measuring the degree of contamination disposed in the flow heater, said sensor including a transmitter element transmitting optical signals and a receiver element receiving optical signals.

2. The household appliance according to claim 1, wherein the flow heater is formed with a connection piece for said sensor.

3. The household appliance according to claim 2, including a receptacle within which the sensor is disposed, said receptacle being introduced into said connection piece of the flow heater.

4. The household appliance according claim 3, wherein said receptacle has a substantially round cross section.

5. The household appliance according to claim 3, wherein said receptacle is formed of milky-transparent material.

6. The household appliance according to claim 3, wherein said receptacle has a completely closed end projecting into the flow heater.

7. The household appliance according claim 1, which further comprises a conductor plate on which said sensor is mounted, said transmitter element and said receiver element being disposed mutually opposite and facing one another on said conductor plate.

8. The household appliance according to claim 3, which further comprises a conductor plate on which said sensor is mounted, and wherein said receptacle is formed with at least one guide for insertingly receiving said conductor plate.

9. The household appliance according to claim 8, wherein said guide is formed with mounting ribs disposed in pairs and at a mutual spacing corresponding to a thickness of said conductor plate.

10. The household appliance according to claim 3, wherein said receptacle is formed with a first leg supporting said transmitter element and a second leg supporting said receiver element, said first and second legs being disposed at a given spacing from one another.

11. The household appliance according to claim 10, wherein said legs have a cross-section corresponding to respective segments of a circle facing one another with respective chords thereof.

12. The household appliance according to claim 10, wherein said legs each has a recess formed therein defining a wall thickness of said receptacle less than a wall thickness of remaining parts of the receptacle.

13. The household appliance according to claim 3, including an O-ring sealing off said receptacle in said connection piece.

14. The household appliance according to claim 3, including a snap connection fastening said receptacle to the flow heater.

15. The household appliance according to claim 14, wherein said snap connection comprises at least one spring tab projecting from said connection piece and having an orifice formed therein for receiving a catching boss of said receptacle.

* * * * *